(12) United States Patent
Lang et al.

(10) Patent No.: US 7,214,806 B2
(45) Date of Patent: May 8, 2007

(54) SYNTHETIC MULTIPLE QUATERNARY AMMONIUM SALTS

(75) Inventors: Weilian Lang, Austin, TX (US); Charles Little, Austin, TX (US); Victor van de Pas, Zaltbommel (NL)

(73) Assignee: Sachem, Inc., Austin, TX (US)

( * ) Notice: Subject to any disclaimer, the term of this patent is extended or adjusted under 35 U.S.C. 154(b) by 514 days.

(21) Appl. No.: 10/795,772

(22) Filed: Mar. 8, 2004

(65) Prior Publication Data

US 2005/0194113 A1  Sep. 8, 2005

Related U.S. Application Data

(60) Provisional application No. 60/550,274, filed on Mar. 5, 2004.

(51) Int. Cl.
*C07D 303/08* (2006.01)
*C07C 211/00* (2006.01)

(52) U.S. Cl. .................. 549/551; 564/290; 564/295; 210/700

(58) Field of Classification Search ........... 549/551; 564/290, 295; 210/700
See application file for complete search history.

(56) References Cited

U.S. PATENT DOCUMENTS

| 4,554,021 | A | 11/1985 | Harvey et al. |
|---|---|---|---|
| 5,616,800 | A | 4/1997 | Roerden et al. |
| 6,177,577 | B1 | 1/2001 | Roerden et al. |
| 6,376,583 | B1 | 4/2002 | Winkler et al. |
| 6,855,819 | B2 | 2/2005 | Likitalo et al. ............ 536/124 |

*Primary Examiner*—Amelia A. Owens
(74) *Attorney, Agent, or Firm*—Renner, Otto, Boisselle & Sklar, LLP

(57) ABSTRACT

This invention pertains to novel multiple quaternary ammonium salts and their derivatives represented by the formula:

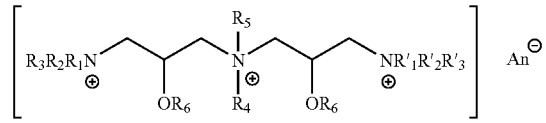

wherein each $R_1$, $R'_1$, $R_2$, $R'_2$, $R_3$, $R'_3$, $R_4$ or $R_5$ is independently selected from the group consisting alkyl, aryl, aralkyl and $-CH_2-CH(OR_6)-CH_2N^+R_1R_2R_3$;

wherein one or more $R_6$ group is selected from the group consisting of:

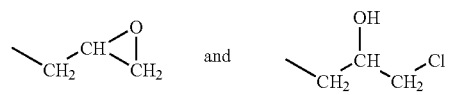

and wherein $An^-$ is an anion.

This invention also pertains to novel multiple quaternary ammonium salts and their derivatives represented by the formula:

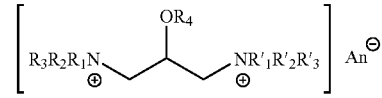

wherein each $R_1$, $R'_1$, $R_2$, $R'_2$, $R_3$ or $R'_3$ group is independently selected from the group consisting of alkyl, aryl, aralkyl and $-CH_2-CH(OR_4)-CH_2N^+R_1R_2R_3$;

wherein one or more $R_4$ group is selected from the group consisting of:

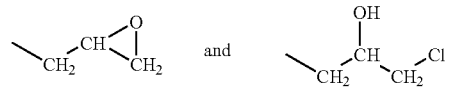

and wherein $An^-$ is an anion.

5 Claims, No Drawings

SYNTHETIC MULTIPLE QUATERNARY AMMONIUM SALTS

This application claims the benefit of the U.S. Provisional Application entitled "Synthetic Multiple Quaternary Ammonium Salts," Application No. 60/550,274, filed Mar. 5, 2004.

BACKGROUND OF THE INVENTION

1. Field of the Invention

The present invention pertains to compositions comprising multiple quaternary ammonium salts (multiple quats), methods of using said compositions, and processes for making said compositions.

2. Description of Related Art

Organic quaternary ammonium salts, also known as tetraorgano ammonium salts, are compounds comprising positively-charged nitrogen atoms. These compounds comprise aliphatic chains, yet nevertheless can be water soluble in some instances.

The positive charge associated with a quaternary ammonium salt ("quat salt" or "multiple quat") is unaffected by changes in pH. That is, the charge on the nitrogen center is not the result of simple protonation of an amine, so the pH of aqueous solutions of these salts may be adjusted over a wide range without causing the loss of the positive charge on the nitrogen center.

Quat salts that contain a group capable of forming a covalent bond with another molecule or with a polymer are sometimes called "cationizing" agents. Such cationizing agents have been used to impart permanent positive charge to polymers. Specifically, cationizing agents containing 2,3-epoxypropyl groups,

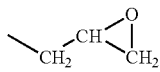

or 3-chloro-2-hydroxypropyl groups,

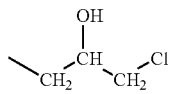

are particularly useful in such applications. In principle, these groups are capable of forming a covalent chemical bond by reaction with many organic functional groups—hydroxyl, thiols, primary and secondary amines, ketones, carboxylic acids, isocynates, substituted ureas, etc.

The present invention concerns cationizing agents containing either a 2,3-epoxypropyl group or a 3-chloro-2-hydroxypropyl group. These cationizing agents also contain two or more positive charges per molecule. Furthermore, these cationizing agents are capable of imparting permanent (as opposed to transient) positive charge to polymers by forming a covalent chemical bond with an appropriate substituent on the polymer.

The resulting "cationized" polymers have found use as flocculants in waste water treatment, as aids in the manufacture of paper, textiles, cements, and detergents, and as components of extrudable composites with epoxy-containing resins (as in U.S. Pat. No. 6,376,583 to Dow Chemical Company).

In certain instances, quaternary ammonium salts having a reactive functionality have been used to create cationic starch derivatives useful as flocculants in wastewater treatment, and in the manufacture of paper, textiles, cements, and detergents.

In some instances, such as in the manufacture of paper from recycled pulp, the cationic charge that can be imparted to starch with known cationizing agents is insufficient to overcome the effect of the high ionic strength processing medium. Furthermore, when sufficient charge can be achieved with known cationizing agents, it sometimes must be done so in a manner that renders that starch particle unacceptable for other reasons (e.g., excessive swelling). Other types of hydroxyl-containing polymers, such as the synthetic polyvinylalcohols, undergo that same cationizing reactions and suffer the same deficiencies in currently known cationizing agents.

U.S. Pat. Nos. 5,616,800 and 6,177,577 disclose dicationic and polycationic monoprimary alcohols. However the disclosed structures are linear and contain a single primary alcohol group at the terminus of the molecule, which may be less desirable features in certain applications.

For the aforementioned reasons, it would be desirable to discover quaternary ammonium salts comprising multiple positively-charged amine groups that have advantageous properties. It would also be useful to discover compounds and methods for making improved cationic carbohydrates for use in a variety of industries.

BRIEF SUMMARY OF THE INVENTION

The present invention provides multiple quat compounds of the general formula

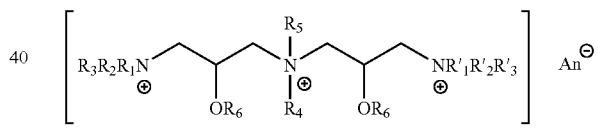

wherein each $R_1$, $R'_1$, $R_2$, $R'_2$, $R_3$, $R'_3$, $R_4$ or $R_5$ is independently selected from the group consisting of alkyl, aryl, aralkyl and $-CH_2-CH(OR_6)-CH_2N^+R_1R_2R_3$; wherein one or more $R_6$ group is selected from the group consisting of:

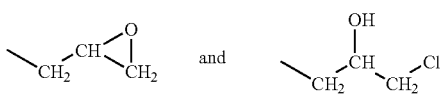

and wherein $An^-$ is an anion.

In certain embodiments, the multiple quat compounds are cyclized such that one $R_1$ group and one $R_4$ group comprise a single alkyl group having one or more carbons. The cyclic structure thus formed by the alkyl-group bridge includes two positively charged nitrogen centers separated by a three-carbon fragment bearing an $-OR_6$ group.

The present invention also provides multiple quat compounds of the general formula:

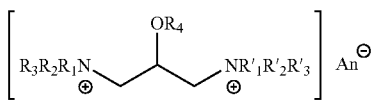

wherein each $R_1$, $R'_1$, $R_2$, $R'_2$, $R_3$ or $R'_3$ group is independently selected from the group consisting of alkyl, aryl, aralkyl and —$CH_2$—$CH(OR_4)$—$CH_2N^+R_1R_2R_3$; wherein one or more $R_4$ group is selected from the group consisting of:

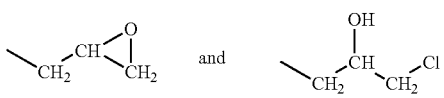

and wherein $An^-$ is an anion.

In certain embodiments, the compounds are cyclized such that one $R_1$ group and one $R'_1$ group comprise a single alkyl group having one or more carbons. The cyclic structure thus formed by the alkyl-group bridge includes two positively charged nitrogen centers separated by a three-carbon fragment bearing an —$OR_4$ group.

The present invention also provides modified carbohydrates formed by the reaction of the multiple quat compounds of the present invention and a carbohydrate having one or more hydroxyl groups. In certain preferred embodiments, the carbohydrate is a starch.

Further the present invention provides methods of making the multiple quat compounds and modified carbohydrates of the present invention and methods of using the modified carbohydrate. For example, the present invention provides methods of using the modified carbohydrate of the present invention as a waste water treatment agent or in papermaking processes.

DETAILED DESCRIPTION OF THE INVENTION

As used herein "composition" includes a mixture of the materials that comprise the composition, as well as, products formed by the reaction or the decomposition of the materials that comprise the composition.

As used herein "derived from" means made or mixed from the specified materials, but not necessarily composed of a simple mixture of those materials. Substances "derived from" specified materials may be simple mixtures of the original materials, and may also include the reaction products of those materials, or may even be wholly composed of reaction or decomposition products of the original materials.

As used herein "halo" refers to a group comprising a halogen, such as chloro, bromo, fluoro, or iodo.

As used herein, "alkyl" refers to a group of carbon and hydrogen atoms derived from an alkane molecule by removing one hydrogen atom. "Alkyl" may include saturated monovalent hydrocarbon radicals having straight, cyclic or branched moieties Said "alkyl" group may include an optional carbon-carbon double or triple bond where said alkyl group comprises at least two carbon atoms. It is understood that for cyclic moieties at least three carbon atoms are required in said alkyl group. Alkyl groups may include any number of carbon atoms, however, for the purposes of the present invention, about 20 or less carbon atoms are preferred. For example, alkyl groups of 2, 3, 4, 5, 6, 7, 8, 9, 10, 11, 12, 13, 14, 15, 16, 17, 18, 19, or 20 carbons may be employed in the present invention. Of course, alkyl groups of longer length may be employed in the present invention. One of ordinary skill in the art, via routine experimentation, following the techniques herein, could synthesize and test molecules containing various alkyl lengths.

As used herein, "aralkyl" refers to a radical in which an aryl group is substituted for a hydrogen atom of an alkyl group. "Aryl" is any simple or substituted aromatic structure such as phenyl, naphthyl, fluorenyl, phenanthryl, etc. Aralkyl groups may include any number of carbon atoms, however, for the purposes of the present invention, about 20 or less carbon atoms are preferred. For example, aralkyl groups of 7, 8, 9, 10, 11, 12, 13, 14, 15, 16, 17, 18, 19, or 20 carbons may be employed in the present invention. Of course, aralkyl groups of more carbon atoms may be employed in the present invention. One of ordinary skill in the art, via routine experimentation, following the techniques herein, could synthesize and test molecules containing various sizes of aralkyl groups.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 and the like, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

As used herein, $An^-$ represents one or more anions associated with the multiple quats of the present invention. The number and total charge of the negatively-charged anions associated with the quaternary ammonium ions of the present invention will vary depending on the pH of the mixture and on the anion of the acid or acids used for neutralization. The anions of the present invention may be any anion known to those of skill in the art, including monovalent, divalent and multivalent anions such as sulfonate, triflate, trifylamide, carboxylate, $F^-$, $Cl^-$, $Br^-$, $I^-$, $ClO_3^-$, $HSO_4^-$, $SO_4^{2-}$, $PO_4^{3-}$, $HPO_4^-$, $BF_4^-$, $PF_6^-$ and the like.

The multiple quats of the present invention comprise one or more compounds. Thus, the multiple quats of the present invention may be a pure compound or may be a mixture of compounds.

Multiple Quats

The multiple quat compounds of the instant invention include those having the chemical structure I:

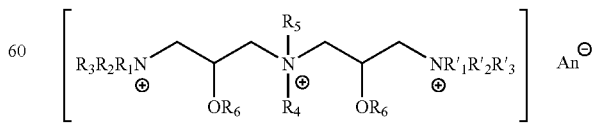

In chemical structure I each group designated $R_1$, $R'_1$, $R_2$, $R'_2$, $R_3$, $R'_3$, $R_4$ or $R_5$, is independently selected from the group consisting alkyl, aryl, aralkyl and —$CH_2$—CH $(OR_6)$—$CH_2N^+R_1R_2R_3$ $An^-$, wherein any $R_1$, $R_2$ or $R_3$ group may be the same or different than the other $R_1$, $R'_1$, $R_2$, $R'_2$, $R_3$ or $R'_3$ groups in the structure, and wherein $An^-$ is one or more anions. $R_4$ and $R_1$ may be covalently bound, thus forming a cyclic structure. This cyclic molecule therefore comprises two positively charged nitrogen centers separated by the three-carbon fragment bearing an —$OR_6$ group. The covalently bound $R_4$ and $R_1$ can comprise a combined total of at least 1 or more carbons. Each group designated $R_6$ can be independently selected from the group consisting of hydrogen, alkyl and aralkyl, however at least one of the $R_6$ groups must be either a 2,3-epoxypropyl group,

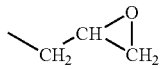

or a 3-chloro-2-hydroxypropyl group,

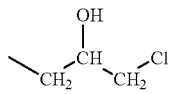

As with the other independently selected groups, any given $R_6$ group may be the same or different than any other $R_6$ group in the structure.

The multiple quat compounds of the instant invention also include those having the chemical structure II:

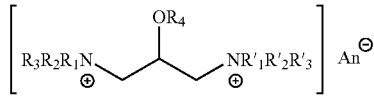

In chemical structure II each group designated $R_1$, $R'_1$, $R_2$, $R'_2$, $R_3$ or $R'_3$ group is independently selected from the group consisting alkyl, aryl, aralkyl and —$CH_2$—$CH(OR_4)$—$CH_2N^+R_1R_2R_3$ $An^-$, wherein any $R_1$, $R_2$ or $R_3$ group may be the same or different than the other $R_1$, $R'_1$, $R_2$, $R'_2$, $R_3$ or $R'_3$ groups in the structure, and wherein $An^-$ is one or more anions. The $R_1$ on one nitrogen and the $R'_1$ on a second nitrogen separated by the central —$CH_2$—$CH(OR_4)$—$CH_2$— fragment can be covalently bound, thus forming a cyclic structure within the molecule comprising two positively charged nitrogen centers separated by the three-carbon fragment bearing an —$OR_4$ group. The covalently bound $R_1$ and $R'_1$ groups can comprise a combined total of at least 1 or more carbons. Each group designated $R_4$ can be independently selected from the group consisting of hydrogen, alkyl and aralkyl, however at least one of the $R_4$ groups must be either a 2,3-epoxypropyl group,

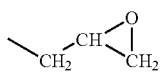

or a 3-chloro-2-hydroxypropyl group,

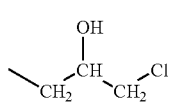

As with the other independently selected groups, any given $R_4$ group may be the same or different than any other $R_4$ group in the structure.

Processes to Make Compounds Having Structures I–II and Mixtures Thereof

Precursors to the cationizing agents can be prepared by a number of processes. Each Process I–V described below yields a hydroxyl-containing multiply charged quat salt that can be transformed into a cationizing agent by reaction of at least one of the hydroxyl groups with epichlorohydrin.

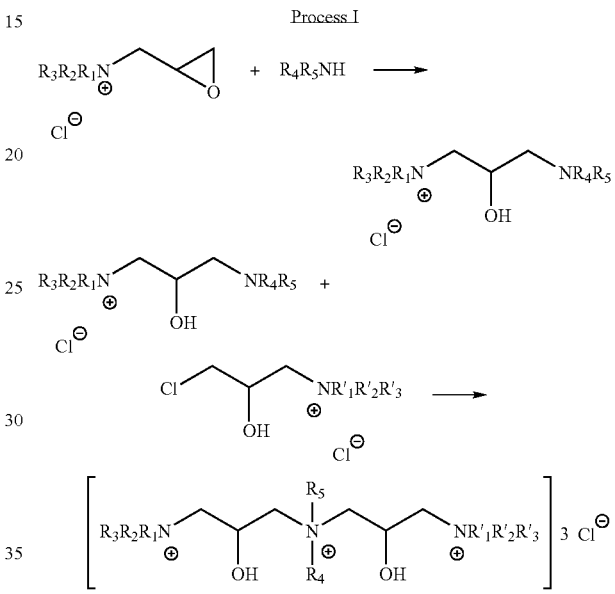

In Process I a secondary amine is allowed first to react with one equivalent of an epoxypropyl quat. This reaction is typically conducted by slow, dropwise addition of an aqueous solution of the epoxypropyl quat to an aqueous solution of the amine at about 25° C., taking care to control the usual exotherm. After several hours of stirring at about 25° C. it is sometimes necessary to heat to between 50° C. and 90° C. for about one hour in order to drive the reaction to completion. The product of this reaction contains a tertiary amine center, which is then allowed to react with one equivalent of a chlorohydrin quat under the same typical conditions as in the previous step. Alternatively, the tertiary amine-containing intermediate can be converted to its hydrochloride salt by addition of hydrochloric acid, and then allowed to react with an epoxypropyl quat.

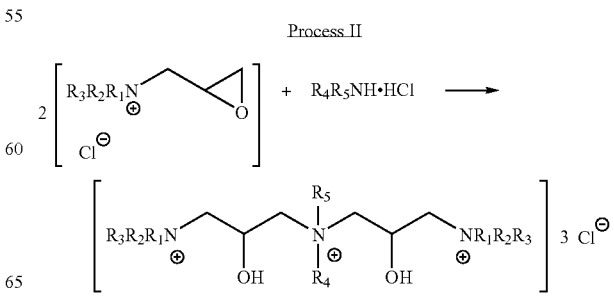

In Process II a secondary amine in its hydrochloride salt form is allowed to react with two equivalents of an epoxypropyl quat under the same typical conditions as in either step in Process I. Unlike the final product in Process I, the final product in Process II is necessarily symmetrical about the central quat group bearing the $R_4$ and $R_5$ substituents. However, in certain embodiments wherein $R_1$, $R_2$ or $R_3$ group is a —$CH_2$—$CH(OR_6)$—$CH_2N^+R_1R_2R_3$ sidechain, the $R_1$, $R_2$ or $R_3$ groups of the sidechain can potentially be the same or different than other $R_1$, $R_2$ or $R_3$ groups in the structure.

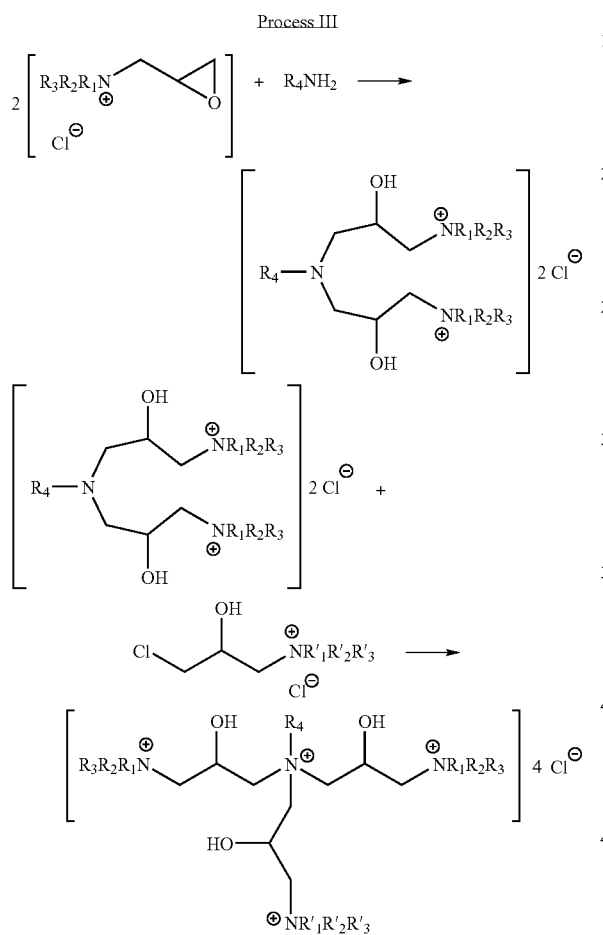

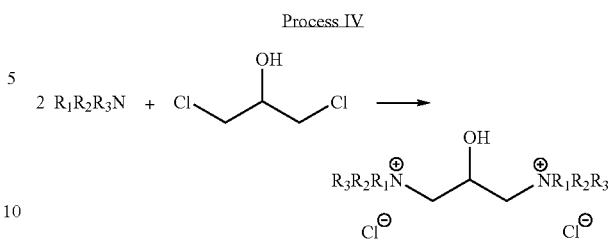

In Process IV two equivalents of a neutral tertiary amine are allowed to react with one equivalent of a 1,3-disubstituted 2-propanol, such as 1,3-dichloro-2-propanol (DCP), wherein the substituted moiety is any good leaving group for an SN2 reaction, e.g. halo groups. The product of this reaction is a diquat alcohol. Alternatively, a di-tertiary amine such as tetramethylethylenediamine may be employed under dilute conditions that will favor cyclization rather than polymerization:

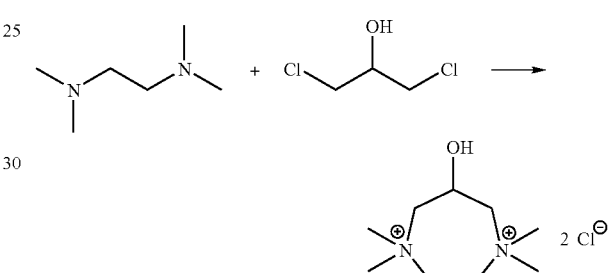

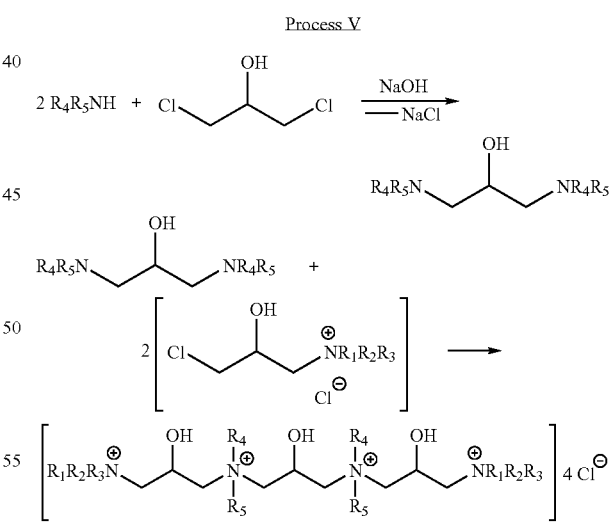

In Process III a primary amine is allowed to react with two equivalents of an epoxypropyl quat under the same typical conditions as in either step in Process I. The product of this reaction contains a tertiary amine center, which is then allowed to react with one equivalent of a chlorohydrin quat under the same typical conditions as in the previous step. The N-substituents ($R'_1$, $R'_2$, and $R'_3$) on the chlorohydrin quat used in the final step may be the same or different than the N-substituents ($R_1$, $R_2$, and $R_3$) on the epoxy quat used in the first step. Alternatively, the tertiary amine-containing intermediate can be converted to its hydrochloride salt by addition of hydrochloric acid, and then allowed to react with an epoxypropyl quat. Also, in certain embodiments wherein $R_1$, $R_2$ or $R_3$ group is a —$CH_2$—$CH(OR_6)$—$CH_2N^+R_1R_2R_3$ sidechain, the $R_1$, $R_2$ or $R_3$ groups of the sidechain can potentially be the same or different than other $R_1$, $R'_1$, $R_2$, $R'_2$, $R_3$ or $R'_3$ groups in the structure.

In Process V two equivalents of a neutral secondary amine are allowed to react with one equivalent of a 1,3-disubstituted 2-propanol, such as 1,3-dichloro-2-propanol (DCP) in the presence of a base to accept the liberated HCl. The product of this reaction is a bis-tertiary amine. This intermediate may then be treated with two equivalents of a chlorohydrin quat. Alternatively, the di-tertiary amine may be used in its dihydrochloride salt form in a reaction with two equivalents of an epoxypropyl quat, as in Processes I–IV. In either case, the product is a tetraquat alcohol.

For each of the compounds described in Process I–V each $R_1$, $R'_1$, $R_2$, $R'_2$, $R_3$, $R'_3$, $R_4$ and $R_5$ group may be the same or different from one another. In certain embodiments of the present invention, all groups sharing a similar designation, i.e. $R_1$, $R_2$, $R_3$, $R_4$ or $R_5$, may be identical chemical groups. In other embodiments, groups sharing a similar designation can differ from one or more other groups sharing that designation, so long as each group is an alkyl group, an aralkyl group or a —$CH_2$—$CH(OR_6)$—$CH_2N^+R_1R_2R_3$ $An^-$ group.

Precursors of cationizing agents containing cyclic structures are known in the chemical literature. For example, 6-member ring structures may be prepared by the methods described in Axenrod, et. al., J. Organic Chemistry, vol. 65, pp 1200–1206 (2000), or Chapman, et. al., U.S. Pat. No. 6,310,204 B1 (2001):

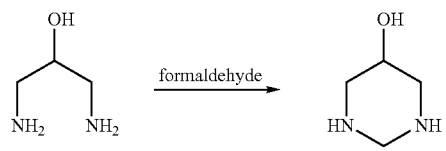

Quaternization of the resulting di-secondary amine is then accomplished by sequential or exhaustive alkylation with an appropriate alkylating agent:

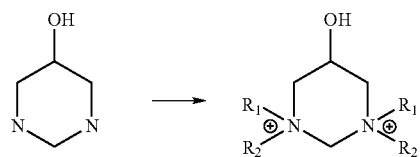

wherein $R_1$ and $R_2$ are as described previously. In a preferred embodiment, the cyclic di-secondary amine would first be transformed to a cyclic di-tertiary amine by reductive alkylation at each nitrogen, then the resulting cyclic di-tertiary amine would be alkylated at each nitrogen with a reactive quaternary ammonium salt, such as (3-chloro-2-hydroxypropyl)trimethylammonium chloride:

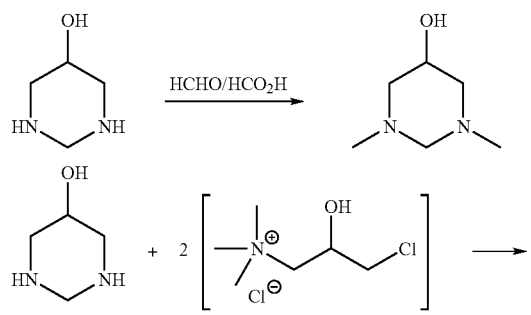

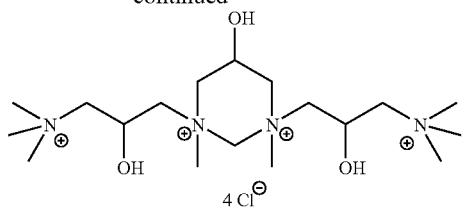

Cyclic diamine precursors containing 7 or more ring atoms can be prepared by two general methods. The first method is cyclization of a 1,3-dihalo-2-propanol with an α,ω-ditosylamide, followed by removal of the tosyl protecting groups, as reported by Saari, et. al. (J. Organic Chemistry, vol. 36, pp 1711–1714 (1971)) or Wu, et. al. (Synth. Communications, vol 25, pp 1427–1431 (1995)):

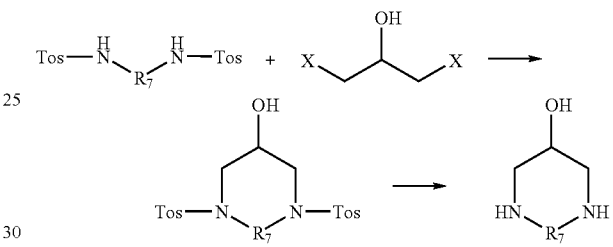

wherein $R_7$=—$CH_2CH_2$—, —$CH_2CH_2CH_2$—, or o-$C_6H_4$, and X=Cl, Br, or I. The α,ω-ditosylamides are conveniently prepared in high yield by the method of Moore, et. al. (WO 94/04485). The free cyclic diamines may be quaternized with appropriate alkylating agents as described previously for the 6-member ring precursors:

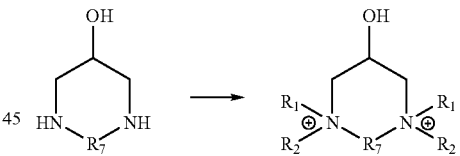

A second known method for preparation of cyclic diamine precursors involves cyclization of a 1,3-dihalo-2-propanol with an α,ω-dibenzylamine, followed by removal of the benzyl protecting groups by hydrogenolysis, as reported by Kanstrup, et. al. (WO 02/02560 A2):

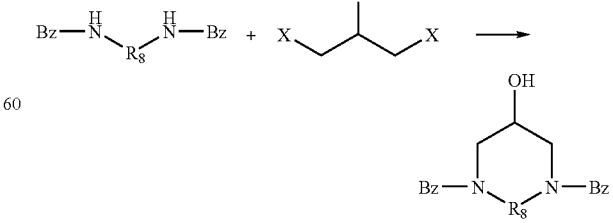

-continued

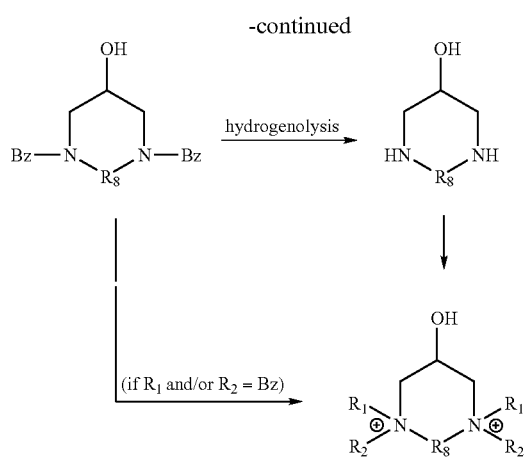

wherein $R_8$=—$CH_2CH_2$—, —$CH_2CH_2CH_2$—, or o-$C_6H_4$, X=Cl, Br, or I, and represents a benzyl group (—$CH_2$—$C_6H_5$). If $R_1$ or $R_2$ in the final product is desired to be a benzyl group, the hydrogenolysis step may be omitted, and the direct cyclization product containing intact benzyl groups may be quaternized by reaction with one equivalent of an alkylating agent.

The hydroxyl-containing quat salts described above are merely precursors to cationizing agents. They can be converted to cationizing agents by derivatization of at least one hydroxyl group in the molecule with epichlorohydrin. Methods for converting a hydroxyl group to a (3-chloro-2-hydroxypropyl)ether or a 2,3-epoxypropyl ether by reaction with epichlorohydrin are well know, and are essentially identical to the methods used to synthesize epoxy resins used in formulating epoxy structural adhesives:

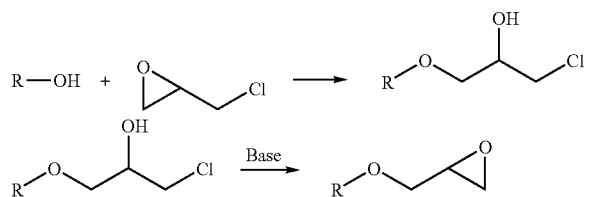

In the scheme above, R represents the remainder of the multiply charged quat salt precursor. Among commercial products made by such well-known chemistry is the diglycidyl ether from the reaction between Bisphenol A and two equivalents of epichlorohydrin. This epoxy resin is known by the trade names D.E.R. 331™ (Dow Chemicals), and Epon® 828 (Resolution Performance Products).

The manner of contacting the (3-chloro-2-hydrroxypropyl)ammonium salts, 2,3-epoxypropylammonium salts, primary, secondary or tertiary amines or amine hydrohalides is not particularly important so long as the desired reaction occurs. Any method of contacting these compounds known to those of skill in the art can be used. Also, the starting compounds are often readily available and, in addition, many syntheses are available to those skilled in the art to make the desired starting compounds.

The mixing conditions may vary depending on the specific compounds employed and the desired product. In most instances, it is acceptable to contact the compounds and the optional solvent at ambient pressure and a temperature high enough for the reaction to occur efficiently but not so high as to decompose or boil off any starting compound.

Characteristics and Uses of Multiple Quats of the Present Invention

The purity of the multiple quats produced by the processes of this invention can often be greater than 90%, preferably 93% or higher, more preferably 95% or higher, most preferably 99% or higher.

In general, multiple quats comprise multiple active hydroxyl groups are useful in the creation of customized compounds or polymers comprising multiple quat monomers. A particularly preferred use for the compounds of the present invention is for the preparation of cationic carbohydrates, particularly cationic starches.

The modified carbohydrate can be any carbohydrate having a hydroxyl group capable of reacting with the reagents of the present invention, including carbohydrate monomers and dimers such as monosaccharides, disaccharides, polyhydroxy aldehydes and polyhydroxy ketones. The modified carbohydrates of the present invention can also comprise carbohydrate polymers including polysaccharides such as starch, cellulose, chitosan, alginate, gum, mucilage, polymeric compounds that can be hydrolyzed to polyhydroxy aldehydes or polyhydroxy ketones, and the like.

Where the carbohydrate is a starch, the starch may come from sources including corn, potato, tapioca, wheat, sago, rice, maize, grain sorghum, waxy sorghum, amaranth, arrowroot, banana, barley, cassava, millet, oat, rye, sweet potato, yam and the like. The starch may be a refined or modified form of starch or may be an unmodified component of a cereal grain. Suitable carbohydrate polymers also include, for example, gums such as gum tracagarth, guar gum, modified guar gum, locust bean cum, galactomannam gum, tamarind gum, karaya, okra, xanthan gum and the like. Cellulose materials, including hemicellulose containing materials such as those derived from hull fibers or cellulose ethers can also be used as carbohydrates of the present invention.

Cellulose ethers are often preferably employed in cementitious and adhesive compositions. Suitable cellulose ethers include methylcellulose, hydroxyethylcellulose, hydroxypropylcellulose, hydroxypropylmethylcellulose, ethylhydroxyethylcellulose, hydroxybutylmethylcellulose, carboxymethylcellulose, carboxymethylmethylcellulose, hydroxyethylhydroxypropylmethylcellulose, hydroxyethylmethylcellulose, hydroxyethylhydroxypropylcellulose and the like.

The carbohydrate material may be selected from the group consisting of unmodified carbohydrate material, chemically modified carbohydrate material such as acid-modified, dextrinized, oxidized, hydrolyzed or derivatized carbohydrate material and the like, carbohydrate ethers and esters which retain reactive hydroxyl sites, and mixtures thereof. Modified carbohydrates can have been treated with acids, alkalis, salts and mixtures thereof as well as enzymes to produce a modified carbohydrate. Alternatively, the carbohydrate can be treated with a derivatizing agent such as sodium tripolyphosphate, propylene oxide, 2,3-epoxypropyl-trimethylammonium chloride, sodium chloroacetate, epoxychlorohydrin, acetic anhydride, maleic anhydride, 2-chloroethyl diethylamine hydrochloride, 2,3-epoxypropyl sulfonate, triethylamine, sulfur trioxide, urea and the like.

Carbohydrates such as starches are commonly classified into these main groups, namely: cationic carbohydrates which will bond to anions, anionic carbohydrate which will bond to cations and amphoteric carbohydrate which will bond to both anions and cations. This invention relates to the preparation of a cationic or amphoteric carbohydrate.

Cationic carbohydrates have numerous commercial uses. Cationic starches, gums and the like, for example, are used in papermaking, textile size, waste water treatment and the like. In particular, cationic starches are widely used as wet end additives in the papermaking process to improve fines and filler retention while increasing the strength characteristics of the resultant paper. A smaller, but no less important, papermaking application is in the size press and coating areas where cationic starches contribute to the strength and surface characteristics of the finished paper and, in addition, reduce the biological oxygen demand contribution of the broke upon repulping.

Cationic carbohydrate polymers are also used for water treatment, particularly flocculation and flotation of suspended solids in the paper, mining, oil drilling and other industries.

The amount of cationic carbohydrate to put to use in applications such as papermaking, textile size, waste water treatment and the like can be determined by routine experimentation, using evaluation methods known to those of skill in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synthesis of a Tetraquat: N,N'-bis[3-[dimethyl(phenylmethyl)ammonio]-2-hydroxypropyl]-2-hydroxy-N,N,N',N'-tetramethyl-1,3-propanediaminium tetrachloride [Expell™ SP, CAS # 415938-92-0]. First, 1,3-dichloro-2-propanol (DCP) was converted to 1,3-bis(N,N-dimethylamino)-2-propanol (DIMAPOL) by reaction with two equivalents of dimethyl amine, essentially as described by Perrine (*J. Organic Chemistry*, vol. 18, pp 1137–1141 (1953)). Then freshly distilled DIMAPOL (146.2 g, 1.0 mole) and approx. 170 mL of water were charged to a round bottom flask fitted with a reflux condenser. Aqueous (3-chloro-2-hydroxypropyl)benzyldimethylammonium chloride (905.7 g @ 59.8% solids=541.6 g=2.05 moles) was added dropwise over a period of 3 hours. The resulting solution was stirred for 11 hours at room temperature. The solution was then heated to 50° C. and held at this temperature for 1 hour with continuous stirring, after which it was allowed to cool to room temperature. The resulting aqueous solution of the tetraquat was bottled and stored in the dark.

EXAMPLE 2

Synthesis of a Triquat: 2-Hydroxy-N-[2-hydroxy-3-(trimethylammonio)propyl]-N,N,N',N'-pentamethyl-1,3-propanediaminium trichloride [DMTQ]. An aqueous solution of 2,3-epoxypropyltrimethylammonium chloride (Aldrich, CAS registry # 3033-77-0) was found by titrametric assay (tetrabutylammonium iodide/perchloric acid method) to contain 72.9 wt % active epoxy species. A solution of dimethylamine hydrochloride (407.75 g, 5.0 moles, Aldrich) in 411 mL water was stirred vigorously in a round bottom flask fitted with a reflux condenser while 1040 g of the epoxypropyl quat salt solution (=758.2 g active=5.0 moles) was added dropwise over about 1 hour with no external heating or cooling. This addition caused no noticeable exotherm. The resulting solution was stirred at room temperature for 1 hour after addition was complete. At this point dropwise addition of another equal portion of the epoxypropyl quat salt solution (5.0 moles) was started. This addition caused a strong exotherm, and continued addition eventually brought the solution to reflux. The rate of addition of this second epoxypropyl quat salt charge was adjusted to keep the exotherm in control. When addition was complete the solution was stirred while it was allowed to cool. When its temperature reached 70° C. (after about 3 hours), external heating was applied with a heating mantle controlled by an electronic controller (J-Kem Electronics) at a setpoint of 70° C. The solution was kept at 70° C. for approx. 24 hours. The solution of DMTQ was allowed to cool to room temperature, bottled, and stored in the dark.

EXAMPLE 3

Synthesis of a Diquat: 2-Hydroxy-N,N,N,N',N',N'-hexamethyl-1,3-propanediaminium dichloride [BTA]. DCP (80 g, 0.62 moles) and 40% aqueous trimethylamine (188 g @ 40 wt %=75.2 g=1.27 moles) were charged to a 500 mL round bottom flask fitted with a reflux condenser. This mixture was heated to 75° C. and held at this temperature with vigorous magnetic stirring for 48 hours. At the end of this time the clear, colorless solution was allowed to cool to room temperature. The yield of BTA was >98%.

EXAMPLE 4

Synthesis of a Cationizing Agent: N,N,N,N',N',N'-Hexamethyl-2-(oxiranylmethoxy)-1,3-propanediaminium dichloride [BTA-GE]. Epichlorohydrin (18.5 g, 0.2 mole, Aldrich) and hexane (100 mL) were charged to a round bottom flask fitted with a reflux condenser. An alkaline solution consisting of BTA (24.74 g, 0.1 mole), NaOH (12 g, 0.3 mole) and 44 g of water was prepared and added dropwise to the epichlorohydrin solution over approx. 30 minutes with vigorous stirring. The addition of BTA solution was begun with all components at room temperature, but the strongly exothermic reaction caused the temperature to rise sharply. The rate of addition was controlled such that at no time did the temperature of the reaction mixture exceed 50° C. Vigorous stirring was continued for 1 hour after addition of the alkaline BTA solution was finished. After the reaction mixture had cooled to room temperature, stirring was stopped and the liquid portion was decanted from the sodium chloride precipitate. The water and hexane layers were separated and the hexane layer was discarded. The water layer was evaporated under reduced pressure. The resulting residue was triturated with 100 mL anhydrous MeOH and additional insoluble sodium chloride precipitate was filtered away. Solvent was evaporated under reduced pressure to yield 32 g of a thick, yellowish liquid. By direct titration of epoxy groups (tetrabutylammonium iodide/perchloric acid method), the crude product was determined to be 91.4% pure (96.4% yield). $^1$H-NMR, $^{13}$C-NMR and mass spectrometry were consistent with the assigned structure.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A compound of the formula

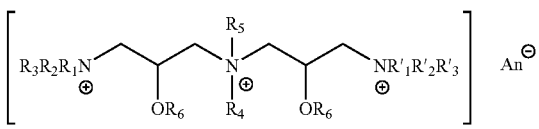

wherein each $R_1$, $R'_1$, $R_2$, $R'_2$, $R_3$, $R'_3$, $R_4$ or $R_5$ is independently selected from the group consisting of alkyl, aryl, aralkyl and —$CH_2$—$CH(OR_6)$—$CH_2N^+R_1R_2R_3$ $An^-$, wherein any $R_1$, $R_2$ or $R_3$ group may be the same or different than other $R_1$, $R'_1$, $R_2$, $R'_2$, $R_3$ or $R'_3$ groups, and wherein each $R_6$ can be independently selected from the group consisting of H, alkyl and aralkyl, a 2,3-epoxypropyl group having the structure:

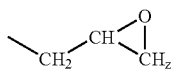

and a 3-chloro-2-hydroxypropyl group having the structure:

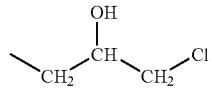

and wherein $An^-$ is an anion, provided that at least one of the $R_6$ groups is the 2,3-epoxypropyl group or the 3-chloro-2-hydroxypropyl group.

2. The compound of claim 1, wherein one $R_1$ group and the $R_4$ group comprise a single alkyl group having one or more carbons, and wherein the alkyl group forms part of a cyclic structure that further comprises two positively charged nitrogen centers separated by a three-carbon fragment bearing an —$OR_6$ group.

3. A compound of the formula

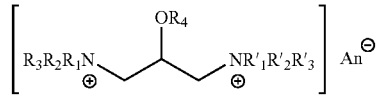

wherein each $R_1$, $R'_1$, $R_2$, $R'_2$, $R_3$ or $R'_3$ group is independently selected from the group consisting of alkyl, aryl, aralkyl and —$CH_2$—$CH(OR_4)$—$CH_2N^+R_1R_2R_3$ $An^-$, wherein any $R_1$, $R_2$ or $R_3$ group may be the same or different than other $R_1$, $R'_1$, $R_2$, $R'_2$, $R_3$ or $R'_3$ groups, and wherein each $R_1$ can be independently selected from the group consisting of H, alkyl and aralkyl, a 2,3-epoxypropyl group having the structure:

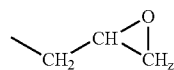

and a 3-chloro-2-hydroxypropyl group having the structure:

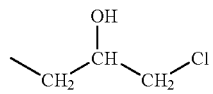

and wherein An– is an anion, provided that at least one of the $R_4$ groups is the 2,3-epoxypropyl group or the 3-chloro-2-hydroxypropyl group.

4. The compound of claim 3, wherein the $R_1$ and $R'_1$ groups comprise a single alkyl group having one or more carbons, and wherein said alkyl group forms part of a cyclic structure that further comprises two positively charged nitrogen centers separated by a three-carbon fragment bearing an —$OR_4$ group.

5. The compound of claim 3 wherein the one or more $R_4$ groups is a 2,3-epoxypropyl group.

* * * * *

UNITED STATES PATENT AND TRADEMARK OFFICE
CERTIFICATE OF CORRECTION

PATENT NO.        : 7,214,806 B2                                    Page 1 of 1
APPLICATION NO.   : 10/795772
DATED             : May 8, 2007
INVENTOR(S)       : Lang et al.

It is certified that error appears in the above-identified patent and that said Letters Patent is hereby corrected as shown below:

Column 16, line 20, replace "$R_1$" with --$R_4$--.

Signed and Sealed this

Twentieth Day of April, 2010

David J. Kappos
*Director of the United States Patent and Trademark Office*